United States Patent [19]

Konoki et al.

[11] 4,231,961
[45] Nov. 4, 1980

[54] PROCESS FOR PREPARATION OF UREA

[75] Inventors: Keizo Konoki, Tokyo; Michio Nobue, Funabashi; Akito Fukui, Yokkaido; Shigeru Inoue, Kamakura, all of Japan

[73] Assignees: Toyo Engineering Corporation; Mitsui Toatsu Chemicals, Incorporated, both of Tokyo, Japan

[21] Appl. No.: 91,444

[22] Filed: Nov. 5, 1979

[30] Foreign Application Priority Data

Nov. 30, 1978 [JP] Japan .................. 53-148131

[51] Int. Cl.³ .......................................... C07C 126/00
[52] U.S. Cl. ........................................... 564/65
[58] Field of Search .................. 260/555 A

[56] References Cited
U.S. PATENT DOCUMENTS

| 3,356,723 | 12/1967 | Kaasenbrood | 260/555 A |
| 3,816,528 | 6/1974 | Cook | 260/555 A |
| 3,936,500 | 2/1976 | Kaasenbrood | 260/555 A |
| 3,944,605 | 3/1976 | Inoue | 260/555 A |
| 4,003,928 | 1/1977 | Heunks | 260/555 A |
| 4,053,507 | 10/1977 | Inoue | 260/555 A |
| 4,066,693 | 1/1978 | Vendebos | 260/555 A |
| 4,081,469 | 3/1978 | Ono | 260/555 A |

Primary Examiner—Brian E. Hearn
Attorney, Agent, or Firm—Blanchard, Flynn, Thiel, Boutell & Tanis

[57] ABSTRACT

In a urea synthesis process, the reaction product from the reaction vessel is flowed in series through high pressure, medium pressure and low pressure decomposing and stripping devices to decompose ammonium carbamate to $NH_3$ gas, $CO_2$ gas and water vapor, and to remove those gases and unreacted starting materials from the aqueous urea solution. $CO_2$ gas is used as the stripping gas in the decomposing and stripping devices.

1 Claim, 1 Drawing Figure

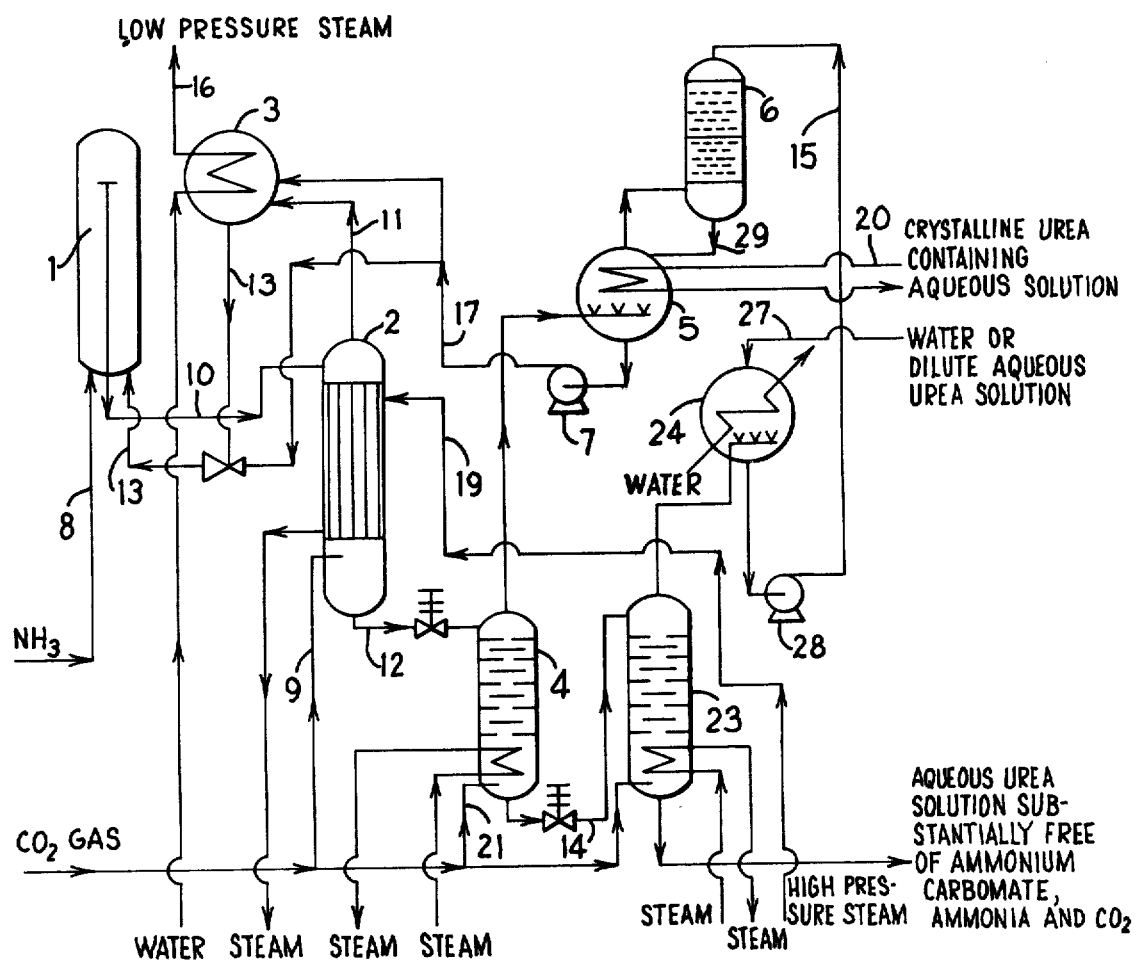

PROCESS FOR PREPARATION OF UREA

The present invention relates to a process for the preparation of urea.

It is a primary object of the present invention to provide an improved urea synthesis process in which unconverted reaction product substances, that is, substances which are not converted to urea, particularly ammonium carbamate, are decomposed at a high efficiency and the decomposition products are returned to the urea synthesis reactor, and wherein the equipment costs and the utility costs (electric power, steam and water) for the total urea synthesis process are reduced.

As is well known, urea is synthesized by reacting $NH_3$ and $CO_2$, as starting materials, under high pressure and high temperature conditions, in the presence of an excess amount of $NH_3$, to form ammonium carbamate and the thus-formed ammonium carbamate is dehydrated to obtain urea.

These reactions are represented by the following two reaction schemes:

$$2NH_3 + CO_2 \rightleftharpoons NH_2COONH_4 \tag{1}$$

$$NH_2COONH_4 \rightleftharpoons NH_2CONH_2 + H_2O \tag{2}$$

In the dehydration reaction represented by the scheme (2), the actual conversion is determined by an attainment ratio of the equilibrium conversion which is variable depending on reaction conditions such as the temperature, the pressure, the residence time and the composition of the starting materials. This conversion is in the range of 50 to 75% when the synthesis is conducted on an industrial scale.

As a method for separating unconverted substances, namely, substances other than urea and water, from the effluent from the reaction vessel, which effluent is a mixture of urea, ammonium carbamate, excess ammonia and water, there has heretofore been adopted a method in which the pressure of the effluent from the reaction vessel is reduced and the effluent is heated to decompose the ammonium carbamate, as the principal unconverted substance, to $NH_3$ and $CO_2$, such $NH_3$ and $CO_2$ are separated in the gaseous state from the urea solution together with the excess $NH_3$, the gaseous mixture of $NH_3$ and $CO_2$ is absorbed in a solution provided at a low pressure, ammonium carbamate decomposing and recovering step subsequent to the high pressure, unconverted product decomposing step and the thus-obtained solution is returned to the reaction vessel.

In this conventional method, since the temperature level during the step of decomposing ammonium carbamate is low, there is caused the disadvantage that the thermal recovery is limited qualitatively and quantitatively. In order to compensate for this disadvantage, the operation conditions in the reaction vessel are controlled so as to maintain the above-mentioned actual conversion at a high level.

As another conventional method, there can be mentioned a method in which the liquid effluent from the reaction vessel is caused to flow in gas-liquid contact with gaseous $NH_3$ or $CO_2$ directly and without reduction of the pressure, in a high pressure decomposing and stripping vessel. Substantially all of the unconverted ammonium carbamate is decomposed and separated from the liquid phase together with the excess $NH_3$, and the separated and recovered gaseous mixture is condensed together with the starting material gas used as the stripping gas and is returned to the reaction vessel. According to this conventional stripping method, the treatment for the decomposition of ammonium carbamate and separation and recovery of the gaseous decomposition products is performed under substantially the same pressure as the pressure in the reaction vessel and the operation temperature in the step of recovering the gaseous mixture formed by the decomposition is high. Therefore, the heat content of the ammonium carbamate at the recovering step can be utilized for the formation of low pressure steam. In this conventional stripping method, the starting steam necessary for the synthesis of urea should be maintained at a higher temperature and pressure than in the first-mentioned, conventional pressure reduction method and the necessary amount of steam is larger than in the first-mentioned pressure reduction method, but since low pressure steam is recovered during the step of decomposition of ammonium carbamate, as pointed out above, the disadvantage that high temperature and high pressure starting steam must be used in a large quantity will be at least partially ameliorated.

According to this conventional stripping method using $NH_3$ or $CO_2$ as a stripping gas, if the temperature in the decomposing and stripping device is not substantially equal to or higher than the temperature in the reaction vessel, decomposition is impossible because of the equilibrium relation. If the operation is carried out at high temperature for promoting decomposition of the unconverted substances, the decomposing and stripping device is subjected to highly corrosive conditions because of the presence of highly corrosive ammonium carbamate maintained at a high temperature. Accordingly, the operation temperature of the decomposing and stripping device is restricted by the corrosion resistance of the material of which the decomposing and stripping device is made and it is not permissible to elevate the operation temperature sufficiently.

Moreover, if the $NH_3/CO_2$ molar ratio in the mixture of $NH_3$, $CO_2$ and $H_2O$ is increased so as to improve the actual conversion to urea, the pressure and temperature in the reaction vessel are increased and also the temperature in the decomposing and stripping device is inevitably elevated.

Therefore, when the conventional decomposing and stripping method is used, the operation temperature in the reaction vessel is maintained at a relatively low level and the $NH_3/CO_2$ molar ratio in the starting material mixture is maintained at a relatively low level. As a result, the conversion achieved in the reaction vessel is low and corresponds to 55 to 60% of the conversion attainable in the first above-mentioned conventional pressure-reducing method.

This fact means that large quantities of unconverted substances and starting materials are present in the high pressure system which includes the reaction vessel, the decomposing and stripping device and the device for dissolving the decomposition gases. In other words, the efficiency of the urea production equipment is reduced. If only the $NH_3$ and $CO_2$ that are present and recycled in the system are taken into account, the formation, decomposition, re-formation and re-decomposition of unconverted products are repeated within a very expensive high pressure system. Low pressure steam of a low economic value is formed as a by-product, in a large quantity, during the formation and re-formation of unconverted products, while high pressure steam of a higher economic value is consumed in a large quantity during the decomposition and re-decomposition of unconverted products and the unconverted products are not converted to the desired urea. Consumption of a large quantity of high pressure steam and formation of a large quantity of low pressure steam as a by-product are disadvantageous from the industrial viewpoint. Formation of a large quantity of low pressure steam that cannot be utilized in the urea production equipment results in a complete energy loss unless a large quantity of low pressure steam can otherwise be used in a different process located in the vicinity of the urea production system, when this conventional decomposing and stripping method is used.

Moreover, the presence and recycling of ammonium carbamate not converted to urea in the expensive high pressure system result in increases of the equipment cost and power expense.

In order to increase the operation efficiency of the urea synthesis process, it is important to improve the conversion to the desired urea product. As means for improving the conversion to urea, there can be mentioned the following methods.

(1) To elevate the operation temperature and pressure in the reaction vessel.
(2) To increase the $NH_3/CO_2$ molar ratio in the starting material mixture fed into the reaction vessel.
(3) To decrease the $H_2O/CO_2$ molar ratio in the starting material mixture fed into the reaction vessel.

As pointed out hereinbefore, in the conventional decomposing and stripping method, the temperature and pressure in the reaction vessel and the $NH_3/CO_2$ molar ratio in the starting material mixture are as low as 180° C., 140 $Kg/cm^2G$ and 2.8, respectively, when the method is carried out on an industrial scale. Accordingly, the conversion to urea is low and the amount of the unconverted product in the effluent from the reaction vessel is very large. Therefore, the quantity of high pressure steam necessary for effecting decomposition of the unconverted product is inevitably increased, and a large quantity of low pressure steam is formed as a by-product during the step of condensing the gaseous mixture formed by the decomposition in order to recycle such decomposition product to the reaction vessel. Increase of the $NH_3/CO_2$ molar ratio is important for improving the conversion to urea. In the conventional decomposing and stripping method, however, because the ratio of decomposition of ammonium carbamate to $NH_3$ and $CO_2$ in the decomposing and stripping device is reduced and the amount of $NH_3$ left in the liquid phase is increased if the $NH_3/CO_2$ molar ratio is increased, good results cannot be obtained, and the use of a large quantity of high temperature, high pressure steam is necessary to eliminate this disadvantage.

In the conventional decomposing and stripping method, decomposition of substantially all of the ammonium carbamate and evaporation of excess $NH_3$ are performed in the decomposing and stripping device which is maintained at a high pressure and the load on the subsequent steps, such as the step of removing unconverted substances from the urea solution, is reduced. Accordingly, in the conventional decomposing and stripping method, reduction of the decomposition and removal efficiency in the decomposing and stripping device by increasing the $NH_3/CO_2$ molar ratio in the reaction vessel results in serious disadvantages.

Therefore, although it is possible to improve the conversion to urea by increasing the $NH_3/CO_2$ molar ratio, this technique cannot be adopted in combination with the conventional decomposing and stripping method.

We have discovered the process of the present invention in which the causes of the major and minor disadvantages involved in the conventional methods are overcome and unexpectedly good results are obtained.

In the process of the present invention, the temperature, pressure and $NH_3/CO_2$ molar ratio in the reaction vessel are maintained at high levels so as to attain a high conversion to urea, the amount of unconverted products present in the reactor effluent is controlled, and the decomposing and stripping treatment and the treatment for condensing and recovering the gaseous mixture formed by the decomposition are performed in a multi-stage manner so that the total load is appropriately distributed to high pressure, medium pressure and low pressure stages, and the amount of low pressure steam of a low value produced as a by-product is remarkably reduced, whereby the operation efficiency of the urea synthesis process as a whole is remarkably improved.

In the process of the present invention, specific urea synthesis conditions, that cannot be adopted in the conventional decomposing and stripping method, are especially chosen and adopted. Also the amounts of unconverted ammonium carbamate and residual excess ammonium in the effluents from the high pressure, medium pressure and low pressure decomposing stripping stages are controlled to specific levels.

In the multi-stage decomposing and stripping process of the present invention, specific amounts of $CO_2$ are introduced into the respective decomposing and stripping devices so as to improve the efficiency of the decomposing of the unconverted product in each of the decomposing and stripping devices of the high pressure, medium pressure and low pressure stages, and to reduce the amount of water in the solution recovered at the step of condensing and recovering the gaseous mixture formed by the decomposition and stripping.

In the process of the present invention, the following conditions should be maintained in the reaction vessel:
(1) A temperature of 180° to 200° C. and a pressure of 150 to 250 $Kg/cm^2G$.
(2) $NH_3/CO_2$ molar ratio of 3.0 to 4.0.

If the above reaction conditions are not maintained in the reaction vessel, the conversion to urea is reduced and the amount of high pressure steam consumed for decomposition in the decomposing and stripping device is increased, resulting in an increase of the urea manufacturing cost.

The effluent from the reaction vessel is introduced in a high pressure decomposing and stripping device at the upper portion thereof. As the high pressure decomposing and stripping device, there can be employed a film type multi-tubular heat exchanger, a plate column type gas-liquid contact apparatus or other conventional gas-liquid contact apparatus. A part of the $CO_2$ gas, intended eventually to be used as a reactant material for the urea synthesis process, is introduced into the high pressure decomposing and stripping device at the lower portion thereof.

The pressure in the high pressure decomposing and stripping device is maintained at the same level as the pressure in the reaction vessel. Accordingly, in the high pressure stage, decomposition is not achieved by reduction of the pressure, but rather, decomposition and separation of the unconverted substances and evaporation and separation of excess $NH_3$ are performed by heating and by the stripping treatment with the $CO_2$ gas. The ratio of decomposition achieved in this high pressure decomposing and stripping device is controlled to be at a level lower than the decomposition ratio achieved in the conventional stripping method, and a predetermined amount of the unconverted substance is left in the effluent from the high pressure decomposing and stripping device. Therefore, the operation temperature for the decomposition and stripping in the high pressure device can be maintained at a level lower than in the conventional stripping method. Therefore, a less costly construction material can be used for making the high temperature and high pressure decomposing and stripping device which is exposed to highly corrosive ammonium carbamate at a high concentration or, alternatively, the useful operating life of the device can be prolonged. Accordingly, a great advantage can be attained with respect to the material of which the high pressure decomposing and stripping device is made.

In the process of the present invention, the reaction conditions in the reactor are controlled so as to obtain a high conversion to urea, and the amount of the unconverted substances supplied to the high pressure decomposing and stripping device can be reduced. Moreover, the decomposition ratio of the unconverted product achieved in the high pressure decomposition and stripping stage is reduced. Therefore, the amount of high pressure steam consumed at this stage can be remarkably reduced, and the disadvantage of loss of energy caused by formation of an excessive amount of low pressure steam, having little or no practical utility, can be moderated or eliminated.

The liquid effluent from the high pressure decomposing and stripping device is introduced into a subsequent medium pressure decomposing and stripping device wherein the operation pressure is maintained at 15 to 25 $Kg/cm^2G$. The pressure of the effluent is thereby reduced and the effluent is heated in the presence of another part of the $CO_2$ reactant gas, which is introduced here as a stripping gas. The unconverted product, that is, ammonium carbamate, is subjected to the second stage decomposition treatment and is separated from the liquid phase.

The $CO_2$ gas introduced into this medium pressure decomposing and stripping stage is effective for reducing the load on the subsequent low pressure decomposing and stripping stage. This $CO_2$ gas also exerts an effect of reducing the amount of water necessary for condensing and recovering the decomposition gas formed at this stage by decomposition of the unconverted product and thereby reducing the amount of water returned to the reaction vessel.

The heat used at this stage is effectively recovered when the decomposition gas formed at this stage is condensed and recovered and the recovered heat can be effectively used for concentration of the aqueous solution of urea that is obtained as the final product.

The effluent from the medium pressure decomposing and stripping stage is introduced into a low pressure decomposing and stripping stage, the pressure of the effluent is reduced and the effluent is heated in the presence of the remainder of the $CO_2$ reactant gas, introduced as a stripping gas, whereby the small amount of remaining unconverted product can be completely decomposed and removed.

In this low pressure decomposing and stripping stage, the $CO_2$ gas exerts the same effects as mentioned above with respect to the medium pressure decomposing and stripping stage.

The heat necessary to be supplied to this low pressure decomposing and stripping stage is supplied from low pressure steam formed as a by-product when the decomposition gas formed at the high pressure decomposing and stripping stage is condensed.

BRIEF DESCRIPTION OF THE DRAWING

The drawing is a flow sheet diagrammatically illustrating the process of the invention.

The process of the present invention will now be described in detail by reference to the drawing.

A stream of $NH_3$ liquid is fed through a pipe 8 and a stream of recovered solution is fed from a high pressure condenser 3 through a pipe 13 into a urea-synthesis reaction vessel 1. In the reaction vessel 1, reaction conditions of a temperature of 180° to 200° C. and a pressure of 150 to 250 $Kg/cm^2G$ are maintained.

In the starting materials fed into the reaction vessel 1, the $NH_3/CO_2$ molar ratio is maintained in the range of 3/1 to 4/1 and the $H_2O/CO_2$ molar ratio is from 0.3/1 to 0.6/1.

The effluent from the reaction vessel 1 is fed through a pipe 10 into the upper portion of a first, high pressure, decomposing and stripping device 2.

A portion of the starting material $CO_2$ gas is introduced into the lower portion of the first, high pressure, decomposing and stripping device 2 through a pipe 9 and is caused to flow upwardly in said device in gas-liquid contact with the effluent from the reaction vessel 1, which effluent is supplied from the pipe 10 and is flowed downwardly in the device 2 in the form of a thin film.

The high pressure decomposing and stripping device 2 is heated by high pressure steam supplied through a pipe 19.

The gas mixture formed and separated by stripping the effluent from the reaction vessel 1 with $CO_2$ gas in the first, high pressure, decomposing and stripping device 2 is removed from the upper end of said device 2 and is introduced through a pipe 11 into the high pressure condenser 3.

A part of the ammonium carbamate present in the effluent from the reactor 1 is decomposed in the first, high pressure, decomposing and stripping device 2. The effluent discharged from the lower end of said first device 2 is fed into a second, medium pressure, decomposing and stripping device 4 through a pipe 12 while the pressure thereon is reduced. In the effluent from the first device 2, the combined content of $NH_3$ and $CO_2$, other than the $NH_3$ and $CO_2$ present in combined form as urea, is adjusted to be 15 to 25% by weight. If this content is lower than 15% by weight, the amount of decomposition achieved in the second, medium pressure, decomposing and stripping device 4 is reduced, and the quantity of heat discharged in the medium pressure condenser 5 is reduced and the amount of heat imparted to the crystalline urea-containing aqueous solution becomes insufficient. If the above content is higher than 25% by weight, the heat removed by the medium pressure condenser 5 becomes excessive and it is wastefully discarded by excessive heating of the cooling water or the like.

In the high pressure condenser 3, the gaseous mixture supplied through the pipe 11 is mixed with the recovered solution supplied through the pipe 17 and is condensed therein to form ammonium carbamate again and to increase the content of ammonium carbamate in the recovered solution. Then, the recovered solution is fed into the reaction vessel 1 through the pipe 13.

Low pressure steam is obtained from the high pressure condenser 3 through the pipe 16, but the amount of this low pressure steam is much smaller than in the conventional method.

In the second, medium pressure, decomposing and stripping device 4, under temperature and pressure conditions of 150° to 170° C. and 15 to 25 $Kg/cm^2G$, respectively, the urea-containing solution (effluent from first device 2) is subjected to a second decomposing and stripping treatment by supplying another portion of the starting $CO_2$ gas through a pipe 21. The urea-containing solution is stripped by that $CO_2$ gas so that the combined content of $NH_3$ and $CO_2$, other than that present in combined form as urea, is further reduced to be in the range of 5 to 15% by weight. The liquid effluent (urea solution) reaching the lower end of the second device 4 is fed to a third, low pressure, decomposing and stripping device 23 through a pipe 14 while the pressure of the urea solution is reduced.

If the operation temperature in the medium pressure decomposing and stripping device 4 is lower than 150° C., the decomposition efficiency is reduced and if the operation temperature is higher than 170° C., the sensible heat of the effluent from the high pressure decomposing and stripping device 2 cannot be effectively utilized and the amount of high pressure steam necessary for heating the medium pressure decomposing and stripping device is increased.

The gaseous mixture formed by decomposition in the second, medium pressure, decomposing and stripping device 4 is introduced into the medium pressure condenser 5, and it is mixed therein with the recovered solution fed from a gas absorber 6 through a pipe 29 and is condensed.

The pressure of the effluent from the medium pressure condenser 5 is elevated by a pump 7 and the effluent is fed into the high pressure condenser 3 through the pipe 17.

The heat content of the gas fed into the medium pressure condenser 5 is transferred to a crystalline urea-containing aqueous solution supplied through a pipe 20.

The gaseous mixture discharged from the upper end of the medium pressure condenser 5 is introduced into the absorber 6 and is collected in the recovered solution fed into said absorber through the pipe 15, and is then returned to the medium pressure condenser 5 through the pipe 29.

The operation temperature in the medium pressure condenser 5 is controlled to be from 80° to 100° C. and the heat is effectively utilized for effecting concentration of the aqueous solution of urea supplied through pipe 20 at the step subsequent to the second decomposing and stripping step.

In the third, low pressure, decomposing and stripping device 23, the liquid effluent from the lower end of the second, medium pressure, decomposing and stripping device 4 is subjected to a third stripping treatment with $CO_2$ gas under temperature and pressure conditions of 100° to 140° C. and 1.5 to 3 $Kg/cm^2G$, respectively, whereby the remaining 3 to 9% by weight of $NH_3$ and 2 to 6% by weight of $CO_2$, other than that present in combined form as urea, are substantially completely decomposed and stripped.

The decomposition gas mixture from the third, low pressure decomposing and stripping device 23 is introduced into a low pressure condenser 24 and is absorbed in water or a dilute aqueous solution of urea fed in through a pipe 27 as an absorbing medium, and the resulting solution is fed to the gas absorber 6 by means of a pump 28.

In the process of the present invention, the actual conversion of $CO_2$ to urea in the reaction vessel 1 is made close to the equilibrium conversion. The amount of high pressure steam required for effecting decomposition and separation of the unconverted products can be minimized according to the present invention, and it is as small as 0.32 ton of steam per ton of produced urea. The minimum consumption of high pressure steam in the conventional method is about 1 ton of steam per ton of produced urea.

Moreover, in the process of the present invention, since some of the unconverted product is allowed to pass into the downstream stages and the operation temperature in the first, high pressure, decomposing and stripping device 2 is relatively low, the amount of $NH_3$ left in the liquid phase is increased and the formation ratio of biuret can be reduced. For example, if the relative value of the biuret formation ratio at 180° C. is assigned the arbitrary value of 100, then the relative value of the biuret formation ratio at 170° C. is 65. Thus, by maintaining a lower temperature in the high pressure device 2, the amount of biuret formed can be reduced.

In the process of the present invention, since the starting $CO_2$ gas intended eventually to be used in the urea synthesis reaction is additionally used as a stripping gas and it is divided and distributed into the respective stages of the multi-stage decomposing and stripping treatment, the content of $H_2O$ in the liquid returned to the reaction vessel 1 is reduced, and therefore, the conversion to urea in the reaction vessel 1 is improved and the internal volume of the high pressure system can be utilized effectively. In this way the amount of water in the reaction vessel can be reduced by about 25% as compared with the amount of water in the reaction vessel in the conventional method.

The numerical values employed and the results obtained in worked embodiments of the present invention will now be described.

EXAMPLE 1

(1) Reaction vessel 1:
   Temperature: 190° C.
   Pressure: 200 $Kg/cm^2G$
   $NH_3/CO_2$ molar ratio: 4
   $H_2O/CO_2$ molar ratio: 0.37
   Conversion of $CO_2$: 72%

(2) First, high pressure, decomposing and stripping device 2:
   Temperature: 175° C.
   Pressure: 200 $Kg/cm^2G$
   Unconverted product content in effluent: 24% by weight (3) Second, medium pressure, decomposing and stripping device 4:
   Temperature: 155° C. (bottom portion)
   Pressure: 17 $Kg/cm^2G$
   Unconverted product content in effluent: 9% by weight (4) Amounts of other materials supplied to the process (per ton of produced urea):
   High pressure steam (25 $Kg/cm^2G$): 0.68 ton
   Cooling water: 50 tons
   Electric power: 142 KWH (5) Amount of steam produced as by-product (5 Kg/cm$^2$G): 0.3 ton

EXAMPLE 2

(1) Reaction vessel 1:
Temperature: 190° C.
Pressure: 180 Kg/cm$^2$G
NH$_3$/CO$_2$ molar ratio: 3.4
H$_2$O/CO$_2$ molar ratio: 0.52
Conversion of CO$_2$: 65%

(2) First, high pressure, decomposing and stripping device 2:
Temperature: 190° C.
Pressure: 180 Kg/cm$^2$G
Unconverted product content in effluent: 17% by weight (3) Second, medium pressure, decomposing and stripping device 4:
Temperature: 155° C. (bottom portion)
Pressure: 17 Kg/cm$^2$G
Unconverted product content in effluent: 9% by weight (4) Amounts of other materials supplied to the process (per ton of produced urea):
High pressure steam (25 Kg/cm$^2$G): 0.72 ton
Cooling water: 52 tons
Electric power: 142 KWH (5) Amount of steam produced as by-product (5 Kg/cm$^2$G): 0.29 ton The embodiments of the invention in which an exclusive property or privilege is claimed are defined as follows:

1. In a process for the preparation of urea, which comprises reacting NH$_3$ and CO$_2$ in a urea-synthesis reaction vessel under high temperature and high pressure conditions, in the presence of an excess of NH$_3$, then decomposing the ammonium carbamate contained in the effluent from the reaction vessel, separating the decomposition products from the effluent together with the excess NH$_3$ returning them to the reaction vessel, and concentrating the aqueous solution of urea obtained after separating the ammoniun carbamate and excess NH$_3$ from the reactor effluent, and then recovering the urea, the improvement which comprises: feeding NH$_3$ and a recovery solution containing NH$_3$, CO$_2$ and water into said reaction vessel and carrying out a urea synthesis reaction at a temperature of 180° to 200° C., under a pressure of 150 to 250 Kg/cm$^2$ gauge, while controlling the compositon of the reactant materials fed into said reaction vessel so that the NH$_3$/CO$_2$ molar ratio is 3.0 to 4.0 and the H$_2$O/CO$_2$ molar ratio is 0.3 to 0.6; feeding the liquid effluent from said reaction vessel and a part of the CO$_2$ gas to be used as a reactant material into a first, high pressure, decomposing and stripping device, the pressure of which is maintained at the same level as the internal pressure of said reaction vessel, and in said first device flowing the liquid effluent from the first reaction vessel in gas-liquid contact with said part of said CO$_2$ gas, while heating said effluent at a temperature of from 170° C. up to the temperature in said reaction vessel to partially decompose the ammonium carbamate present in said effluent and to strip the gaseous decomposition products thereof and excess NH$_3$ from the liquid by means of said CO$_2$ gas, and separately discharging from said first device a first stream of gas comprised of NH$_3$, CO$_2$ and water vapor, and a high pressure liquid effluent having a total content of 15 to 25% by weight of NH$_3$ and CO$_2$ based on the total weight of the high pressure liquid effluent and excluding NH$_3$ and CO$_2$ present in combined form as urea; reducing the pressure of the high pressure liquid effluent and introducing the high pressure liquid effluent into a second, medium pressure, decomposing and stripping device in which the temperature is maintained at 150° to 170° C. and the pressure is maintained at 15 to 25 Kg/cm$^2$ gauge, and feeding another part of CO$_2$ to be used as a reactant material into said second device as a stripping gas, and in said second device flowing the liquid effluent from said first device in gas-liquid contact with said another part of said CO$_2$ gas to decompose more of the ammonium carbamate and to strip the gaseous decomposition products thereof by means of said another part of said CO$_2$ gas, and separately discharging from said second device a second stream of gas comprised of NH$_3$, CO$_2$ and water vapor, and a medium pressure liquid effluent having a total content of 5 to 15% by weight of NH$_3$ and CO$_2$ based on the total weight of the medium pressure liquid effluent and excluding NH$_3$ and CO$_2$ present in combined form as urea; reducing the pressure of the medium pressure effluent and then introducing same into a third, low pressure, decomposing and stripping device in which the temperature is maintained at 100° to 140° C. and the pressure is maintained at 1.5 to 3 Kg/cm$^2$ gauge and feeding the remainder of the CO$^2$ gas to be used as a reactant material into said third device as a stripping gas, and in said third device flowing the liquid effluent from said second device in gas-liquid contact with said remainder of said CO$_2$ gas to complete the decomposition of the ammonium carbamate and to strip the gaseous decomposition products thereof by means of said remainder of said CO$_2$ gas, and separately discharging from said third device a third stream of gas comprised of NH$_3$, CO$_2$ and water vapor, and a low pressure liquid effluent which is an aqueous solution of urea substantially free of ammonium carbamate, free NH$_3$ and free CO$_2$; then concentrating the effluent from said third device; cooling the third stream of gas discharged from said third device and dissolving same in an aqueous solvent to form a recovery solution; then increasing the pressure of said recovery solution; then dissolving the second stream of gas discharged from said second device in said recovery solution and flowing said recovery solution in indirect heat exchange contact with an aqueous urea solution to concentrate same; then increasing the pressure of said recovery solution and dissolving the first stream of gas discharged from said first device in said recovery solution and flowing said recovery solution in indirect heat exchange contact with water to generate low pressure steam; and then introducing the recovery solution containing dissolved therein the first, second and third streams of gas into said reaction vessel together with the starting NH$_3$ to effect the urea synthesis reaction.

* * * * *